United States Patent [19]

Genese

[11] 4,171,698

[45] Oct. 23, 1979

[54] PREFILLED TWO-COMPARTMENT SYRINGE

[75] Inventor: Joseph N. Genese, Waukegan, Ill.

[73] Assignee: Abbott Laboratories, North Chicago, Ill.

[21] Appl. No.: 824,463

[22] Filed: Aug. 15, 1977

[51] Int. Cl.$^2$ ............................................. A61M 5/00
[52] U.S. Cl. .............................. 128/218 M; 128/272.1
[58] Field of Search .......... 128/218 M, 218 P, 218 N, 128/218 NV, 215, 216, 272.1, 220, 221

[56] References Cited

U.S. PATENT DOCUMENTS

| | | | |
|---|---|---|---|
| 1,234,582 | 7/1917 | Trueblood | 128/218 M |
| 1,279,069 | 9/1918 | Yoshida | 128/218 M |
| 2,841,145 | 7/1958 | Epps | 128/218 M |
| 2,869,543 | 1/1959 | Ratcliff et al. | 128/218 M |
| 3,370,754 | 2/1968 | Cook et al. | 128/218 M X |
| 3,477,432 | 11/1969 | Shaw | 128/218 M |
| 3,570,486 | 3/1971 | Engelsher | 128/218 M |
| 3,724,460 | 4/1973 | Gomez et al. | 128/272.1 X |
| 3,785,379 | 1/1974 | Cohen | 128/218 M |

*Primary Examiner*—John D. Yasko
*Attorney, Agent, or Firm*—Robert L. Niblack; Neil E. Hamilton

[57] ABSTRACT

A prefilled, ready to use, disposable syringe wherein a fluid medicament and a diluent therefor are sealed in two separate telescoping syringe barrels. A medicinal powder is sealed in an outer barrel adjacent the nozzle section by means of a pierceable stopper and the diluent is sealed in an inner barrel between another pierceable stopper and a plunger stopper. A double-pointed cannula is positioned between the two pierceable stoppers by means of a telescoping guide arrangement. Movement of the plunger stopper inwardly in the inner barrel initially effects a piercing of both pierceable stoppers and intermixing of the medicinal powder with the diluent. Continued movement of the plunger stopper will expel the mixed medicament from the syringe.

16 Claims, 11 Drawing Figures

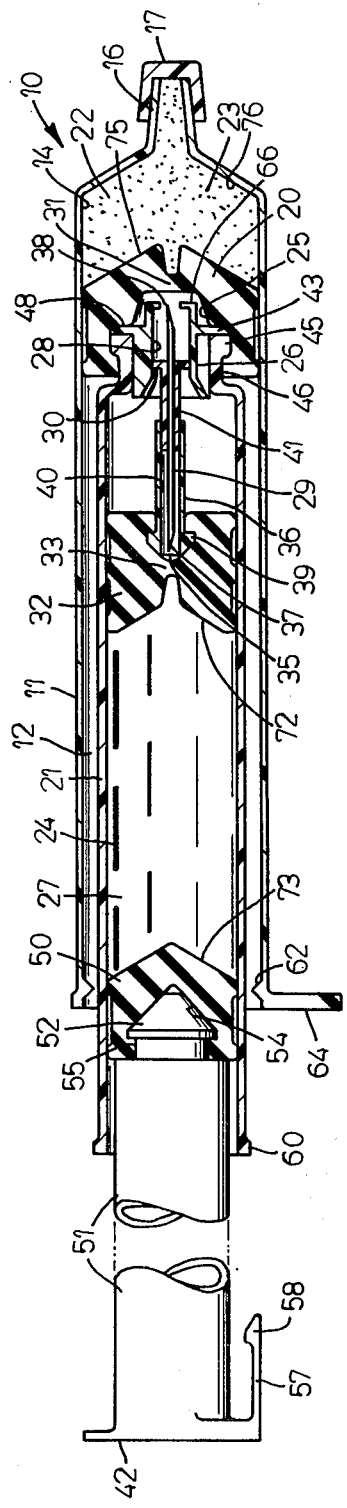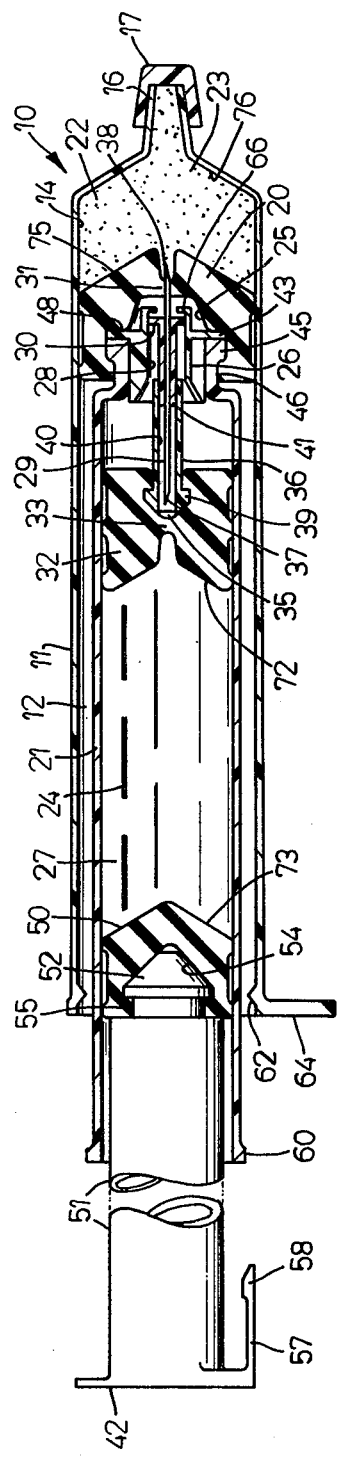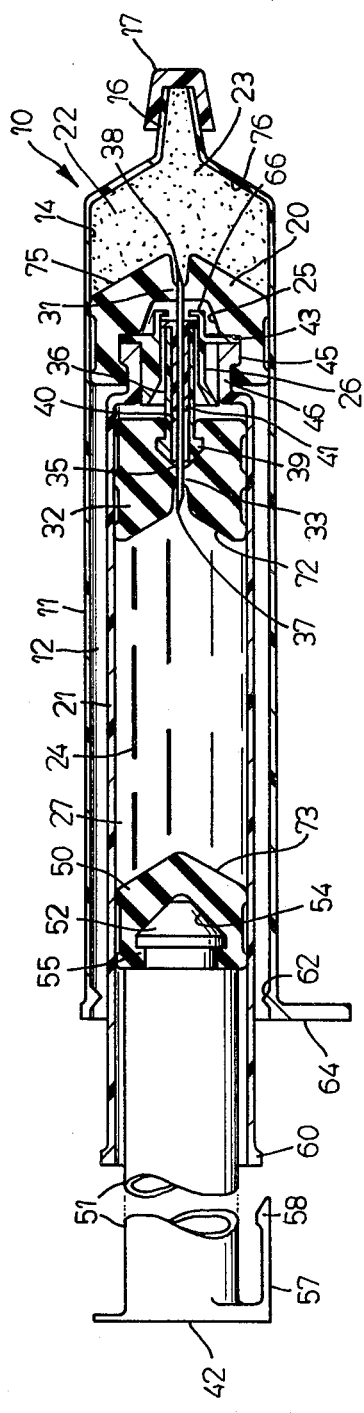

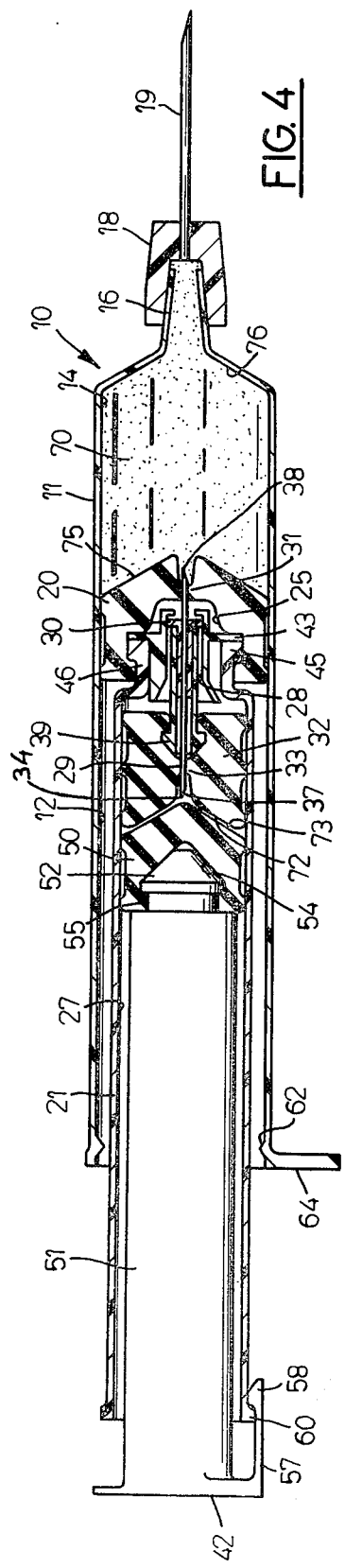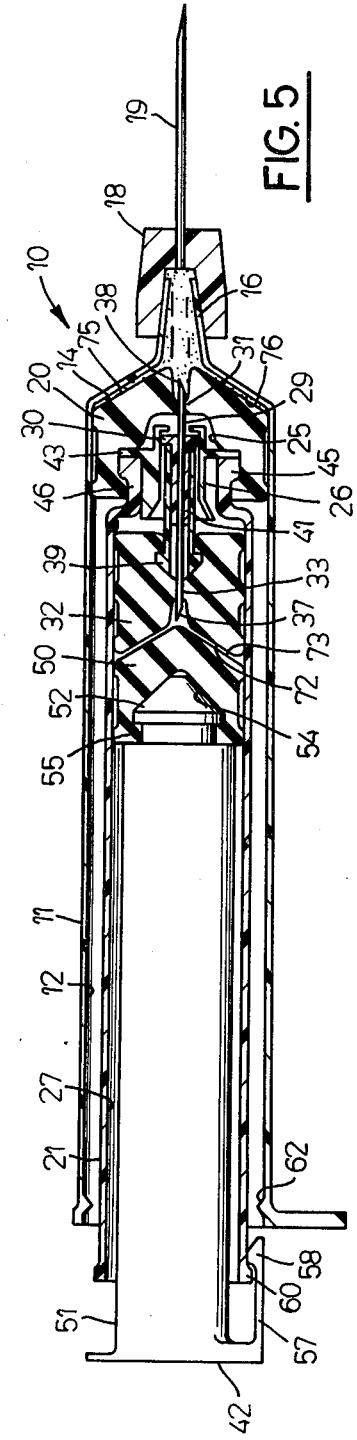

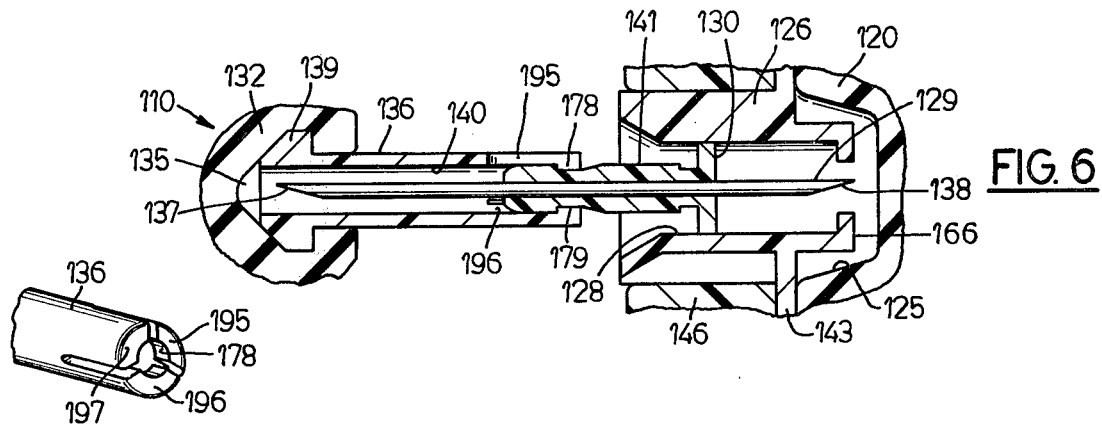
FIG. 6
FIG. 6a
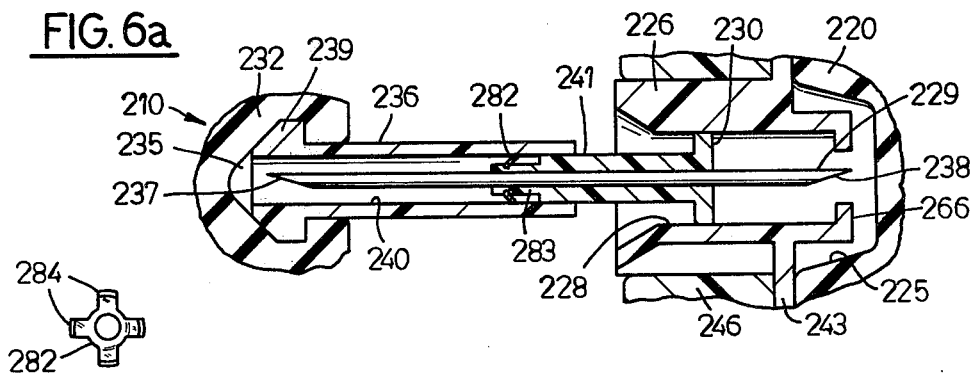
FIG. 7
FIG. 7a
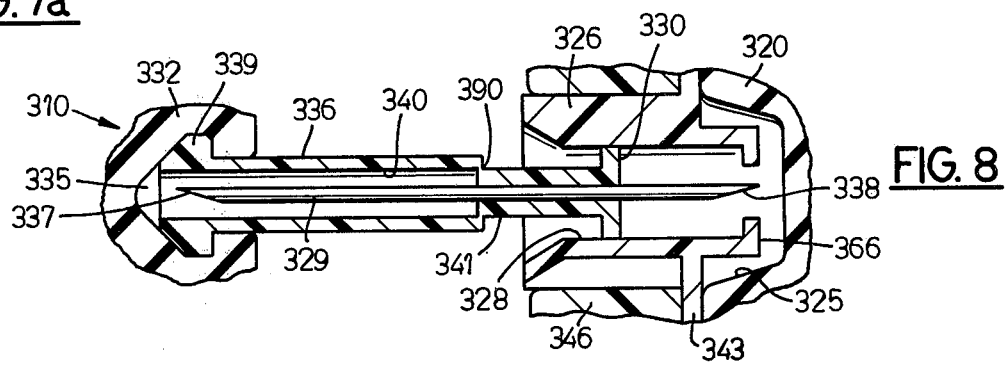
FIG. 8
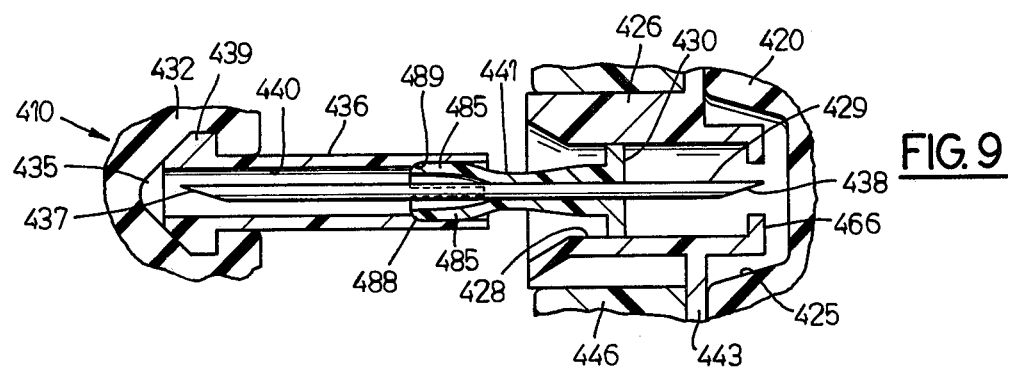
FIG. 9

PREFILLED TWO-COMPARTMENT SYRINGE

BACKGROUND OF THE INVENTION

This invention relates to a disposable syringe of the prefilled type. More particularly it relates to a prefilled, disposable syringe wherein the medicament contained in the syringe is held under isolated maximum sterile conditions until it is desired to premix it with a diluent material, the syringe being completely preassembled and affording positive piercing sequencing by means of a piercing tubular member which is positioned in a telescoping guide member between two sealing stoppers which separate the compartments for the diluent and the medicament.

There are currently available many types of disposable syringes wherein a medicament is sealed in the syringe barrel to be later combined with a diluent for the material in the syringe barrel. There are also available unitary containers which contain a medicament and a diluent for it in two different compartments which are then intermixed prior to their usage. However, many of these devices which are now available either do not afford positive intermixing between the two materials, are costly to manufacture because of the necessity of utilizing many component parts, are complicated in their usage because of many parts being involved or after intermixing in a container still require a syringe for injection. For example, in U.S. Pat. Nos. 2,684,068; 3,098,483 and 3,327,710, combination hypodermic syringes and mixing containers are disclosed. However, these units do not afford complete separation of one of the materials to be mixed from the piercing cannula or tube so that sterility and complete mixing can be a problem. Further, many of these units as well as one of the units described in U.S. Pat. No. 3,542,023 do not afford positive engagement and sequencing of the various compartments for the components to assure their intermixing.

Positive intermixing is also a factor in U.S. Pat. Nos. 3,724,460 and 3,636,950 which while employing a multitude of components still do not afford a positive sequencing action in one unit. In U.S. Pat. Nos. 3,489,147 and 3,477,432, multicomponent combination mixing and administration syringes are disclosed. However, various manipulations of these units must be made in order to activate them.

Further, in U.S. Pat. No. 3,895,633, a specifically designed friction-type sliding fitment is provided for actuation of a needle through a pierceable stopper. In U.S. Pat. No. 4,014,330, a double-pointed cannula is anchored in a sliding member for piercing through two stoppers, one of which is contained in a slidably receivable vial. None of the prior art previously discussed provides a preassembled syringe unit having an inner barrel member within an outer barrel and a telescoping-type piercing action of a double-pointed cannula to interconnect the two chambers within the syringe.

It is an advantage of the present invention to provide a novel preassembled mixing and hypodermic syringe which affords maximum isolation and sterility of two components which are to be ultimately mixed, and positive sequencing of the intermixing. Other advantages are a syringe which is completely preassembled, a syringe which utilizes a unique telescoping arrangement of the double-pointed cannula for piercing through the two stoppers in the syringe separating the two components, a syringe which requires a minimum of manipulative steps for actuation and a minimum amount of space for packaging.

SUMMARY OF THE INVENTION

The foregoing advantages are accomplished and the shortcomings of the prior art are overcome by the present prefilled, readily activated and disposable syringe which has a first barrel member and a second barrel member constructed and arranged to move longitudinally within the first barrel. A first puncturable sealing element engages the internal wall of the first barrel member and is spaced from the nozzle portion to provide a compartment for a first flowable medicinal material. The first puncturable sealing element is interconnected to the second barrel member and a second puncturable sealing element is slidably positioned in the second barrel member and spaced therefrom. A plunger stopper is spaced from the second pierceable sealing element to provide a second chamber for a liquid diluent for the flowable medicinal material in the first chamber. A piercing tubular member having oppositely disposed piercing points is held in a nonoperative position between the first and the second piercing elements and guide means are associated with the second pierceable sealing element to slidably receive the piercing tubular member and afford a sequential piercing of the two pierceable stoppers upon movement of the plunger stopper toward the pierceable stoppers. In a preferred manner, the double-pointed piercing member is secured in a guide block for slidable contact within a guide passage in the first pierceable stopper and also provides a guide surface for the guide means secured to the second pierceable stopper. The pierceable stoppers as well as the plunger stopper are designed so that substantially all of the contents of the syringe can be expelled therefrom. Further, an interlock system is afforded between the plunger rod and the inner barrel member in conjunction with the first pierceable stopper so as to afford an aspirating effect in the syringe if desired.

BRIEF DESCRIPTION OF THE DRAWING

A better understanding of the prefilled, readily activated syringe of this invention will be afforded by reference to the drawing wherein:

FIG. 1 is a view in vertical section showing the hypodermic syringe of this invention in a packaged condition.

FIGS. 2 and 3 are similar to FIG. 1 showing the unit in the next stages of operation.

FIG. 4 is a view similar to FIG. 1 showing the syringe unit with the two components completely mixed together and the syringe ready for injection.

FIG. 5 is a view similar to FIG. 1 showing the syringe unit after the components have been injected.

FIGS. 6-9 are partial views in vertical section showing alternative embodiments of the telescoping arrangement of the double-pointed cannula member for piercing the two pierceable stoppers in the syringe unit.

DESCRIPTION OF THE PREFERRED EMBODIMENT

The prefilled, readily activated syringe generally 10 is composed of the usual barrel 11 forming a tubular chamber 12 with internal wall 14. A nozzle member 16 extends from one end of the syringe barrel and is covered by a removable cover or cap 17. As best seen in FIG. 4, when cap 17 is removed it is replaced by a hypodermic needle 19 which by means of an adapter 18 is positioned on nozzle 16. Disposed in barrel 11 and in sealing engagement with wall 14 is a puncturable sealing element 20. Sealing element 20 is spaced from nozzle 16 to provide a compartment 22 for a flowable medicinal agent 23, preferably in the form of a powder. As seen in FIGS. 1 and 2, sealing element 20 has a chamber 25 for accommodating a bushing 26, with bushing 26 providing a guide passageway 28. A second barrel member 21 is accommodated within barrel 11 and is secured in puncturable sealing element 20 by means of annular portions 45 and 46 extending from barrel 21 and sealing element 20, respectively, and at the same time secure the bushing 26 in chamber 25 by means of shoulder 48.

Slidably received in barrel 21 is a second puncturable sealing element 32 which has a chamber 35 for accommodating head 39 of tubular guide means 36. Disposed in guide 36 is a double-pointed piercing cannula 29 secured to a guide block member 41 for slidable movement of guide 36 thereover. Block 41 terminates in a guide flange 30 for movement in guide passageway 28 of bushing 26. Piercing cannula 29 has two opposing piercing points 37 and 38 for piercing through reduced puncturable areas 31 and 33 of pierceable stoppers 20 and 32, respectively. Also reciprocally disposed in second barrel 21 is a plunger stopper 50 which as spaced from puncturable sealing element 32 provides a compartment 27 for diluent 24. A plunger rod 51 having a head 52 is secured in the stopper 50 by means of chamber 54 and an annular portion 55 extending from stopper 50. Disposed at the opposing end of rod 51 is a latch member 57 terminating in a latch head 58 for engagement with annular projection 60 carried by inner barrel 21. Similarly, a V-shaped stop member 62 extends from barrel 11 and serves as a resistant stop to the removal of puncturable sealing element 20. A finger grip 64 also projects from outer barrel 11.

It will be noted in all of the figures and particularly in FIGS. 4 and 5, that plunger stopper 50 is provided with a projecting convex surface 73 which is accommodated in concave surface 72 of pierceable stopper 32. Similarly, stopper 20 has a convex surface 75 which is accommodated by concave end wall 76 of outer barrel 11.

FIGS. 6-9 illustrate various modifications for slidably attaching the slide block such as 41 of cannula 29 in guide 36. Similar numbers are used to indicate similar parts except that they are designated in the "100", "200", "300" and "400" series. In the FIG. 6 unit, it will be noted that tubular guide means 136 extending from sealing element 132 terminates in opposing finger gripping members 195 and 196 which have flanges such as 178 for temporary engagement in annular groove 179 of guide block 141. As best seen in FIG. 6a, tubular guide 136 is composed of three finger gripping members 195, 196 and 197. In the FIG. 7 syringe unit 210, a star ring 282 is disposed on a stem portion 283 of slide block 241 for frictional engagement inside of tubular guide means 236. As best seen in FIG. 7a, star ring 282 is provided with projections 284 to provide the necessary frictional engagement. In the FIG. 8 unit 310, tubular guide means 336 and the guide block 341 are initially formed as one unit with guide block 341 attached by a breakaway portion 390 and of a diameter to allow guide bore 340 to slide over guide block 341. In the syringe unit 410 in FIG. 9, constricting fingers 485 are disposed at one end of guide block 441 for releasable engagement from increased diameter section 488 and shoulder 489 for subsequent slidable engagement of bore 440 over guide block 441.

OPERATION

A better understanding of the advantages of the readily activated syringe units 10, 110, 210, 310 and 410 will be had by a description of the manner of their operation. Referring to syringe unit 10, it will be packaged as shown in FIG. 1. The medicinal material 23 will in this instance be a powdered, flowable material such as a general anesthetic. It will be noted that the medicinal material will be held in a sterile condition by means of puncturable sealing element 20 and sealing cap 17. A liquid diluent 24 will similarly be held in a sterile condition as it will be sealed between pierceable stopper 32 and plunger stopper 50. If desired, the entire syringe unit could be packaged in a sterile overwrap such as composed of sterile paper or aluminum laminate.

When it is desired to utilize unit 10, all that is required is the movement of plunger rod 51 inwardly into the second barrel 21 which is facilitated by placement of a finger around finger grip 64 with the thumb on the end portion 42 of the plunger rod. This will move plunger stopper 50 from a position shown in FIG. 1 to that shown in FIG. 2. With this movement, guide block 41 will have been carried by frictional engagement with tubular guide means 36 and guide flange 30 will travel along guide passageway 28 in bushing 26 to a position where the piercing point 38 will have penetrated through reduced puncturable area 31 in pierceable stopper 20. It will be recognized that the frictional resistance between guide block 41 and guide means 36 will be sufficient so as to effect nonsliding relationship during penetration of stopper 20. Movement of the piercing member 29 will continue in the direction of nozzle 16 until guide 30 will abut against stop portion 66 of bushing 26. At this point, and with continued movement of plunger stopper 50 inwardly to a position shown in FIG. 3, point 37 of piercing member 29 will penetrate through the reduced puncturable area 33 of stopper 32 and assume a position as shown in FIG. 3. Communication will now be effected between compartment 27 and compartment 22. Continued movement of the stopper 50 inwardly into barrel 21 will cause the fluid diluent to flow through piercing member 29 into compartment 22 and at the same moment cause stopper 20 to back away from the nozzle portion 16 as compartment 22 becomes filled with the fluid to result in a combined diluent and medicament mixture 70. This is best seen in FIG. 4.

The syringe unit 10 is now ready for administration at which time the cap 17 will be removed from nozzle 16 and a hypodermic needle 19 by means of an adapter 18 will be attached. At this stage it should also be recognized that latch member 57 with head 58 will have engaged the annular projection 60 on the inner barrel 21. Accordingly, if it is desired to aspirate the syringe in order to determine if proper injection has been made, this can be effected, as any outwardly pulling action on the plunger rod 51 will simultaneously cause a similar action on the second barrel 21 and sealing element 20 further recognizing that complete removal of stopper 20 from outer barrel 11 will be hindered by means of stop 62. Injection of the medicinal material 70 will be effected in the usual manner with stopper 50 being moved against stopper 32 to cause barrel 21 to move longitudinally in barrel 11. This will cause the medicinal material 70 to be expelled through hypodermic needle 19 until the syringe unit will assume a position as shown in FIG. 5. It will be noted in conjunction with this particular FIGURE that substantially the entire contents of the syringe will be expelled through the concave surface 72 of stopper 32 and the complementary convex surface 73 of plunger 50. Similarly, the convex surface 75 of stopper 20 and the concave configuration of wall 76 of barrel 11 affords the same substantial displacement of the contents of the syringe unit. Point 37 of cannula 29 will be accommodated in chamber 34 so that it will not interfere with the partial interfitting of stoppers 50 and 32.

The functioning of syringe units 110, 210, 310 and 410 in FIGS. 6-9 will be substantially the same as previously indicated for unit 10 in the initial retention of guide block 41 in bore 40 of tubular guide means 36 during puncture of sealing element 20 and subsequent sliding of the tubular guide thereover for later puncture of sealing element 32. In FIG. 6, the retention is first effected by the engagement of finger gripping members 195, 196 and 197 with flanges 178 in annular groove 179 of guide block 141 with subsequent movement of the finger gripping members over block 141 and block 141 into bore 140. In FIG. 7, this initial retention and subsequent sliding action is afforded by means of star ring 282 with projections 284 engaging the bore 240 of tubular guide means 236. In FIG. 8, the initial retention of the guide bar 341 will be accomplished through the breakaway portion 390 which upon further force will become fractured at this point and will then cause a sliding action of tubular guide 336 over guide block 341. Compression of constricting fingers 485 and 486 in unit 410 will cause a similar initial retention of guide block 441 and subsequent sliding of tubular guide 436 thereover as the fingers move from the increased diameter section 488 and away from shoulder 489 into bore 440.

In conjunction with the previously described embodiments, it will be recognized that the needle 19 with adapter 18 could be placed on the nozzle at the time the unit is packaged as shown in FIG. 1. However, the needle will then have to have a tight sealing cap to cover it and there is the risk that powdered material could gain entry to the needle and not become uniformly mixed with a diluent or solvent prior to administration. Alternatively, a spring loaded needle member could be utilized, such as generally indicated in U.S. Pat. No. 3,825,003, to pierce through a diaphragm section separating the powdered material from the needle after the syringe unit is sequenced to the position as shown in FIG. 4.

The preferred materials for composing barrels 11 and 21 are polypropylene and glass, respectively. However, they could both be formed from other clear or translucent plastic materials. Plunger rod 51 with latch 57 is formed from a resinous plastic material with stoppers 20, 32 and 50 being formed from a resilient pierceable rubber or plastic material. Tubular guide means 36, 136, 236, 336 and 436 are preferably formed from a polyester material. Guide blocks 41, 141, 241, 341 and 441 can be conveniently fabricated from a polyvinyl chloride material and tubular piercing member is fabricated from stainless steel.

It will thus be seen that through the present invention there is now provided a prefilled, readily activated, sterile syringe system which can be packaged in a ready-to-use manner and involves a minimum number of manipulative steps for utilization. A medicament material and a diluent therefor, which when intermixed result in a unstable product, are retained in a sterile condition in an isolated manner. Positive, sequential operation of the dual component syringe system is afforded to effect mixing of the medicament and the diluent. The syringe unit can be fabricated without extensive molding operations and can be assembled in a convenient manner and retained in a sterile condition.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

I claim:

1. A prefilled, readily activated syringe comprising:
   a first barrel member defining a substantially tubular chamber having an internal wall portion;
   means defining a nozzle member communicating with said tubular chamber and adapted to receive a hypodermic needle;
   a first puncturable sealing element in sealing engagement with said internal wall of said barrel member and spaced from said nozzle section to provide a compartment for a first flowable medicinal material;
   a second barrel member constructed and arranged to move longitudinally within said first barrel member;
   said first sealing element operatively associated with said second barrel member;
   a second puncturable sealing element slidably positioned in said second barrel member and spaced from said first sealing element;
   a piercing tubular member having oppositely disposed piercing points;
   first guide means operatively associated with said second puncturable sealing element; and
   second guide means operatively associated with respect to said first puncturable sealing element, said first guide means constructed and arranged to telescopingly receive a portion of said second guide means with said piercing tubular member positioned by said first and second guide means;
   a plunger stopper adapted to receive a plunger rod in slidable and sealing engagement in said second barrel member and spaced from said second sealing element to provide a compartment for a second flowable medicinal material;
   whereby upon movement of said plunger stopper in the direction of said second puncturable sealing element, said second puncturable sealing element will in turn move in the direction of said first puncturable sealing element, so that said piercing tubular member will pierce through both said puncturable sealing elements and provide fluid communication between said medicinal materials; upon further movement of said plunger stopper toward said second sealing element, said second flowable medicinal material will flow into said compartment with said first medicinal material and be combined therewith with movement of said first sealing element away from said nozzle section; and upon further movement of said plunger toward said second sealing element substantially all of said medicinal materials will be expelled from said syringe.

2. The prefilled, readily activated syringe as defined in claim 1 wherein said first puncturable sealing element defines a reduced puncturable area and a guide passageway adjacent said puncturable area and said piercing tubular member includes a guide member for slidable contact with said guide passageway.

3. The prefilled, readily activated syringe as defined in claim 2 wherein said second puncturable sealing element defines a reduced puncturable area and said guide means is positioned adjacent said puncturable area.

4. The prefilled, readily activated syringe as defined in claim 3 wherein said guide passageway defined by said first puncturable sealing element includes a chamber and bushing member positioned in said chamber, and said piercing tubular member includes an annular contacting portion for slidable engagement in said bushing member.

5. The prefilled, readily activated syringe as defined in claim 4 wherein said second puncturable sealing element defines a chamber and said guide means is positioned in said chamber.

6. The prefilled, readily activated syringe defined in claim 5 wherein said second sealing element has a reduced wall thickness and said guide means is positioned to direct one of said points of said piercing tubular member through said reduced wall thickness.

7. The prefilled, readily activated syringe as defined in claim 6 wherein said chamber defined by said second sealing element is formed in a generally T-shaped configuration and said guide means is defined by a tubular member having a generally T-shaped head portion positioned in said chamber and receiving said piercing tubular member.

8. The prefilled, readily activated syringe as defined in claim 4 wherein said annular contacting portion for slidable engagement in said bushing member is formed in part by an additional guide block fixed to said piercing tubular member and telescopingly engaging said guide means operatively associated with said second sealing element.

9. The prefilled, readily activated syringe as defined in claim 8 wherein said bushing member includes a flange portion and said first sealing element and said second barrel member includes annular interfitting end portions for securing said flange portion of said bushing in said first sealing element chamber.

10. The prefilled, readily activated syringe as defined in claim 9 wherein said second sealing element and said plunger stopper are constructed and arranged to fit partially one within the other.

11. The prefilled, readily activated syringe as defined in claim 10 wherein said reduced puncturable area is formed in part in said second sealing element by a compartment, so that one of the piercing points is housed in said compartment after puncture of said reduced area.

12. A prefilled, readily activated syringe which can intermix two fluid materials which when combined are unstable and expel substantially all of said intermixed materials comprising:
a first barrel member defining a substantially tubular chamber having an internal wall portion;
means defining a nozzle member communicating with said tubular chamber and adapted to receive a hypodermic needle;
a first puncturable sealing element in sealing engagement with said internal wall of said barrel member and spaced from said nozzle secction to provide a compartment for a first flowable medicinal material;
said first sealing element having an end portion of substantially the same configuration as said nozzle section so as to fit therein in a nesting manner;
a second barrel member constructed and arranged to move longitudinally within said first barrel member;
said first sealing element secured to said second barrel member;
a second puncturable sealing element slidably positioned in said second barrel member and spaced from said first sealing element;
a piercing tubular member having oppositely disposed piercing points;
first guide means operatively associated with said second puncturable sealing element; and
second guide means operatively associated with respect to said first puncturable sealing element, said first guide means constructed and arranged to telescopingly receive a portion of said second guide means, said piercing tubular member received in said second guide means;
a plunger stopper adapted to receive a plunger rod in slidable and sealing engagement in said second barrel member and spaced from said second sealing element to provide a compartment for a second flowable medicinal material;
said plunger stopper and the surface of said second sealing element proximate to said plunger stopper having complementary surfaces for nesting together;
so that when said plunger stopper is moved in the direction of said nozzle section, said piercing tubular member will pierce through both said sealing elements and said medicinal materials will mix together; and upon further movement of said plunger stopper toward said nozzle member said plunger stopper will nest in said second sealing element and said first sealing element will nest in said nozzle section, whereby substantially all of said medicinal materials will be expelled from said syringe.

13. The prefilled, readily activated syringe as defined in claim 12 further including interlocking means operatively associated with said plunger rod and said second barrel member and positioned with respect to said plunger rod and said second barrel member to engage when said plunger stopper engages said second sealing element.

14. The prefilled, readily activated syringe as defined in claim 13 wherein said first barrel member includes a stop member for engagement with said first sealing element.

15. The prefilled, readily activated syringe as defined in claim 14 wherein said first flowable medicinal material is in the form of a powder and said second medicinal material is in the form of a liquid.

16. The prefilled, readily activated syringe as defined in claim 15 wherein all of the components except said piercing member are formed from a resinous plastic material.

* * * * *